United States Patent
Maison-Blanche et al.

(10) Patent No.: US 8,116,859 B2
(45) Date of Patent: Feb. 14, 2012

(54) ELECTROCARDIOLOGIC DEVICE FOR THE ASSISTED DIAGNOSIS OF BRUGADA SYNDROME OR EARLY REPOLARIZATION SYNDROME

(75) Inventors: Pierre Maison-Blanche, Paris (FR); Fabrice Extramiana, Saint-Maur de Fossés (FR)

(73) Assignee: ELA Medical S.A.S., Montrouge (FR)

( * ) Notice: Subject to any disclaimer, the term of this patent is extended or adjusted under 35 U.S.C. 154(b) by 707 days.

(21) Appl. No.: 12/255,529

(22) Filed: Oct. 21, 2008

(65) Prior Publication Data
US 2009/0137916 A1 May 28, 2009

(30) Foreign Application Priority Data

Oct. 24, 2007 (FR) ...................... 07 07441

(51) Int. Cl.
*A61B 5/07* (2006.01)
(52) U.S. Cl. ......................... 600/516; 607/25
(58) Field of Classification Search .................. 600/508, 600/509, 515, 516; 607/18, 25, 26
See application file for complete search history.

(56) References Cited

U.S. PATENT DOCUMENTS

| | | | |
|---|---|---|---|
| 5,113,869 A * | 5/1992 | Nappholz et al. ............. | 600/508 |
| 7,221,976 B2 | 5/2007 | Couderc et al. | |
| 7,297,114 B2 | 11/2007 | Gill et al. | |
| 7,524,287 B2 | 4/2009 | Bharmi et al. | |
| 2007/0038138 A1 | 2/2007 | Gill et al. | |

FOREIGN PATENT DOCUMENTS

| | | |
|---|---|---|
| CN | 1953705 | 4/2007 |
| EP | 0472411 | 2/1992 |
| EP | 1486166 | 12/2004 |
| EP | 1543770 | 6/2005 |
| EP | 1752094 | 2/2007 |
| FR | 2784035 | 4/2000 |
| WO | WO 2006/081336 | 8/2006 |

OTHER PUBLICATIONS

Mutsuo Kaneko, et al., *Automated detectrion of Brugada-type electrocardiogram using diagnostic criteria of the European Society of Cardiology and the American Heart Association*, Science Direct, Journal of Electrocardiology 38 (2005) 96-99, www.elsevier.com/locate/jelectrocard.

Charles Antzelevitch, et al., *Brugada Syndrome: Report of the Second Consensus Conference*, Circulation 2005; 111; 659-670, American Heart Association, Dallas, TX.

(Continued)

*Primary Examiner* — Brian T Gedeon
(74) *Attorney, Agent, or Firm* — Orrick Herrington & Sutcliffe, LLP (57) ABSTRACT

Electrocardiologic device for assisted diagnosis, preferably for the diagnosis of Brugada syndrome or Early Repolarization syndrome. This device allows characterizing the ventricular repolarization wave of an ECG signal collected from a patient. Extracting out of the ECG signal, for each heart beat, an ST segment is constituted of a succession of samples of the ventricular repolarization wave, taken within a time window ([$Q_{ON}$+80 ms, $Q_{ON}$+140 ms]) of a predetermined duration spreading from a moment of window onset defined by a time offset applied to a predetermined temporal origin given by the moment ($Q_{ON}$) of appearance of the QRS complex, whose time position is determined on the ECG signal for each heart beat. Quantizing computes an elevation index compared to a predetermined reference level (BL), and analyzing over a succession of heart beats the persistence and/or variation of this elevation index.

24 Claims, 4 Drawing Sheets

OTHER PUBLICATIONS

Michael Haïssaguerre, M.D., *Sudden Cardiac Arrest Associated with Early Repolarization*, The New England Journal of Medicine, May 8, 2008.

Institut National De La Propriete Industrielle, *Rapport De Recherche Preliminaire*, FR 0707441, Mar. 6, 2008.

* cited by examiner

FIG_1

FIG_2

FIG_3

FIG_4

FIG_5

FIG_6

FIG_7

FIG_8

ELECTROCARDIOLOGIC DEVICE FOR THE ASSISTED DIAGNOSIS OF BRUGADA SYNDROME OR EARLY REPOLARIZATION SYNDROME

FIELD OF THE INVENTION

The present invention is related to electrophysiology, and more particularly to the diagnosis of heart rhythm disorders based on characterizing the ventricular repolarization wave (T wave) of a collected ECG signal from a patient.

BACKGROUND OF THE INVENTION

The ECG signal may be collected through different known techniques: through electrodes applied on the patient's skin and connected to an external recorder, from an implanted device provided with electrodes for collecting a subcutaneous ECG, or through reconstruction of the ECG signals based upon intracardiac EGM signals collected by an implanted device. In all these techniques, the ECG signal is conventionally sampled and digitized so as to be further automatically analyzed, or displayed on a screen to a practitioner.

Several devices have been proposed in the known Prior Art that are specifically directed to analyzing the T wave. See, for example, French patent FR2784035 (commonly assigned herewith to ELA Medical), which discloses detecting the appearance of an ischemic state, and then the evolution of said state in real-time in order to rapidly obtain a reliable predictor for fibrillation or ischemia in the patient. Another example is described in European patent EP 1,486,166 and its U.S. counterpart U.S. Pat. No. 7,221,967 (commonly assigned herewith to ELA Medical), proposing a device aimed at evaluating the "alternans", which is a very small repetitive variation from one beat to the next, in the range of one millivolt, of the ECG waveform within the time window corresponding to the repolarization wave; the presence of such a phenomenon reveals a non-uniform repolarization of the myocardium and constitutes a very good predictor of fibrillation, and therefore of the clinical risk for ventricular arrhythmia and sudden death.

Another parameter of the T wave that can be worth analyzing is the ST segment elevation. The quantization of this phenomenon notably provides a key-index in the diagnosis of the pathology known as "Brugada syndrome". This pathology, of a genetic origin, is characterized by anomalies of the ST segment leading to a high risk of ventricular arrhythmia and sudden death. Its expressions usually appear in adults, with a high risk, notably in patients of Asian origin in their forties, of sudden death by ventricular fibrillation, usually occurring during their sleep, and without any antecedents of syncope or cardiac arrest. It is desirable to be able to quantify the anomalies of the ST segment, and identify, among the patients carrying this syndrome, those presenting a high probability for the occurrence of ventricular arrhythmiae and sudden death, so as to be able to propose them a preventive treatment, notably though implanting an implantable defibrillator.

Is it usually assumed that Brugada syndrome is characterized by an elevation of the ST-segment higher than 200 µV on the precordial derivations, appearing on at least two of these derivations (cf. Antzelevitch et al., *Brugada Syndrome: Report of the 2$^{nd}$ Consensus Conference,* Circulation 2005; 111:659-670).

A similar syndrome, even though its deep causes and concerned populations are different, is named "Early Repolarization Syndrome" (ERS), or "Haïssaguerre syndrome." Its symptoms (notably: syncopes and ST-segment elevation), as well as its complications (notably: sudden death) are identical to those of Brugada syndrome. One can preferably refer to: Haïssaguerre et al., *Sudden Cardiac Arrest Associated with Early Repolarization,* New England Journal of Medicine 2008; 358:2016-2023.

These two syndromes, which concern different populations, are both of genetic origin, even though the genes directly involved in ERS have not yet been isolated.

Various techniques have been proposed so far, for quantizing the ST segment elevation, whether based upon ECG recordings printed on paper ribbons (the most common technique in current clinical practice), or upon digitized ECG recordings. Most practitioners interpret the ECG by using the grid of the paper ribbon and a ruler for quantizing the elevation of the ST segment in patients presenting high risks. As it can be easily understood, such a visual and manual interpretation of the ST segment elevation is subjected to a wide variability from one patient to another, and in addition its analysis is time-consuming and does not allow detecting fine variations of the ST segment.

The article of Kaneko et al., *Automated Detection of Brugada-Type Electrocardiogram Using Diagnostic Criteria of the European Society of Cardiology and the American Heart Association,* Journal of Electrocardiology 38 (2005) 96-99, describes a technique for the automatic evaluation of the ST segment elevation, but through the mere analysis of the rest ECG, and based upon a time reference which is not accurately determinable, that is: the J point, i.e. the point of junction between the QRS complex and the ST segment of the heart wave.

Another method for analyzing the ST segment elevation is described in European patent application EP 1,752,094 and its U.S. counterpart US 2007/0038138, however this is used for the purpose of characterizing acute renal failure through the analysis of the electrogram collected by a cardiac implant on the basis of various parameters including (but not limiting to) the ST segment elevation. PCT patent application WO 2006/081336 and its U.S. counterpart U.S. Pat. No. 7,297,114 describe a similar technique used for the purpose of discriminating a state of cardiac ischemia from a situation of hypo- or hyper-glycemia, also susceptible to affect the ST segment elevation.

OBJECTS AND SUMMARY OF THE INVENTION

Broadly, the present invention relates to an electrocardiologic device for automatic quantizing of the ST segment elevation on the right precordial ECG derivations, through a technique that minimizes any biased interpretation by the practitioner, with a high sensitivity, in the range of 10 µV, and providing an immediate overview of the analyses performed on the ST segment.

As it will be described in the following description, one aspect of the invention is directed to a device allowing to:
reliably quantify the anomalies of an electrocardiogram observed on the ST segment in patients presenting a risk of Brugada syndrome or Early Repolarization syndrome;
balance the indications provided by the device as a function of secondary parameters such as patient's heart rhythm, his/her level of activity, time of the day (awake/sleep, having a meal, . . . );
provide graphical displays allowing the practitioner to get an immediate overview of the evolution and long-term trends of a severity index of the pathology;

follow up the effects of various treatments prescribed to the patient, for example, the administration of an anti-arrhythmic substance, on the level of seriousness of the pathology, in order to assess the relevance of this prescription and eventually adapt posology.

Although mainly described in the context of diagnosing Brugada syndrome or ERS, it should be understood that the present invention is in no way restricted to these specific applications, but rather that it also might be used for other types of diagnosis, insofar as such diagnosis invoke a characterization of the ST segment of an ECG signal.

In the case of the diagnostic of Brugada syndrome (or ERS), in addition to the multiplicity of criteria and the requirement to validate some annex criteria, one first difficulty lies in the fact that the ST segment anomaly which is characteristic of Brugada syndrome (or ERS) is not expressed in a permanent manner. It is therefore necessary to process long periods of the ECG signal in order to detect this type of particular morphology of the T wave.

Another difficulty lies in the fact that the commonly accepted definition of the characteristic anomaly of the ST segment is based upon an "elevation" of this segment, therefore a voltage parameter (in ordinate on the recording), with no actual precise definition of the time origin (in abscissa on the recording) used as a reference for the performed measurements. Particularly, as it will be explained in the following, the "J point" corresponding to the junction between the QRS complex and ST segment, is often not easily identified on the recording, and may also vary, on a time point of view, from one derivation to the other.

The techniques described in US 2007/0038138 and WO 2006/081336, referred to above, are directed to detecting some other types of pathologies, do not allow solving this particular difficulty.

In order to palliate this difficulty, Kaneko et al. (article cited above) propose to "average" the position of the J point on the basis of plural derivations, but that is an approximation which on a practical point of view, leads to major uncertainties, not predictable on the obtained final results.

It should be understood that, the present invention is directed to operating a diagnosis of phenomena of transmembranous nature, as opposed to phenomena related to sick cells as in the case of pathologies such as renal failure or cardiac ischemia. Indeed, the pathologies related to Brugada syndrome or ERS, which manifest in healthy hearts, are caused by "channelopathies", or dysfunctions of the ionic channels.

It should be understood that it is not a purpose of this invention to characterize, for instance, an ischemic state or renal failure state, and follow the evolution thereof over time. But it is, however, one purpose of this invention to ensure a prevention and/or diagnosis of the sudden death, in patients who most of time do not present any particular symptom.

In order to achieve the previously cited goals cited, one preferred embodiment of the present invention proposes an electrocardiologic device for assisted diagnosis and characterization of the ventricular repolarization wave of an ECG signal collected from a patient and preliminarily sampled and digitized, of the general type described in US 2007/0038138 cited above, and including:

extracting means for isolating from the ECG signal, for each heart beat, an ST segment constituted by a succession of samples of the ventricular repolarization wave, taken within a time window of a predetermined period starting from a moment of window onset, defined by a time offset applied to a predetermined time origin;

quantizing means for computing an elevation index of said segment compared to a predetermined reference level; and means for analyzing over a succession of heart beats, the persistence and/or variation of said elevation index.

In a manner that is characteristic of this invention, the predetermined time origin is the moment of appearance of the QRS complex, and the device further comprises means for determining the time position of this point on said ECG signal for each heart beat.

Some advantageous subsidiary characteristics of this invention are as follows. In one embodiment, the offset applied to the predetermined temporal origin ranges from between 60 and 100 ms, and is more preferably 80 ms. Further, the predetermined width of the time window ranges from between 50 and 80 ms, and is more preferably 60 ms.

In another embodiment, the quantizing means further comprises means for making up a matrix providing, for a series of samples ($S_i$) taken within the time window, the amplitude ($V_i$) of corresponding samples of the ECG signal. More preferably, the series of samples is a subset of the samples of said succession of samples of the ventricular repolarization wave. Even more preferably, In addition, the device optionally may include means for concurrently analyzing a plurality of ECG signals coming from different derivations, and means for applying to the matrix a mathematical transform among the group comprising: principal component analysis, Karhunen-Loeve transform, and derivative calculation.

Preferably, the device quantizing means further comprises integrating means for computing the surface area defined by the ECG signal over the width of said time window, for determining the elevation index.

Preferably, too, the device analyzing means comprises means for evaluating an average level of the elevation index based upon at least one of: during a given duration and over a given number of heart beats, and for analyzing the long term variations of the elevation index around this average level. More preferably, the analyzing means comprises classifying means for distributing into a plurality of classes, the successive values of said elevation index collected based upon at least a given duration and a given number of successive heart beats, said distribution into classes being operated as a function of a parameter measured by the device or known thereby, and analyzing at least one among the group consisting of the persistence and the variation of the elevation index, separately for each class. In this embodiment, the parameter is preferably one selected from among the group comprising of: heart rate, RR interval, diurnal nocturnal or prandial of the moment of analysis, the patient's level of activity, the patient's body temperature, the natural or paced nature of the heart beat, the sinusal or extrasystolic character of the heart beat, the existence of a drug treatment.

In yet another embodiment, the analyzing means comprises means for the follow-up of voltage variations within the analysis window, able to search within the ST segment, the presence of a coved pattern that is characteristic of a Brugada syndrome or Early Repolarization Syndrome.

Further, the device optionally may include a graphical display of the variations along time of said elevation index. Also, the analyzing means is preferably able to provide information of assisted diagnosis comprising a risk marker. The risk marker is preferably provided when the elevation index computed by the quantizing means is greater than a predefined threshold during a predetermined duration. In one aspect, the information comprising a risk marker is provided when the elevation index computed by the quantizing means is greater than a predefined threshold over a given number of heart beats. In another, the information comprising a risk marker is provided when the elevation index computed by the quantizing means is greater than a predefined threshold during a predetermined duration and over a given number of heart beats. Preferably, the device is able to concurrently analyze a plurality of ECG signals coming from different precordial derivations, and the information comprising a risk marker is provided when the elevation index computed by said quantizing means is greater than a predefined threshold during a predetermined duration, for ECG signals coming from at least two out of said precordial derivations. Alternately, the device is able to concurrently analyze a plurality of ECG signals coming from different precordial derivations, and the information comprising a risk marker is provided when the elevation index computed by said quantizing means is greater than a predefined threshold over a given number of heart beats, for ECG signals coming from at least two out of said precordial derivations. In another embodiment, the device is able to concurrently analyze a plurality of ECG signals coming from different precordial derivations, and the information comprising a risk marker is provided when the elevation index computed by said quantizing means is greater than a predefined threshold during a predetermined duration and over a given number of heart beats, for ECG signals coming from at least two out of said precordial derivations.

Another aspect of the invention is directed to a device that is an external recorder able to be connected to external electrodes for collecting cutaneous ECG. Yet another aspect of the invention is directed to a device that is an implanted device provided with electrodes for collecting subcutaneous ECG. Yet a different aspect of the invention is directed to a device that is an implanted device able to be connected to electrodes for collecting intracardiac or epicardiac EGM signals, said device further comprising means for reconstructing ECG signals based upon said collected EGM signals. More preferably, the device is an implanted device of the pacemaker, defibrillator or pacemaker/defibrillator or resynchronization device, said device further comprising means for delivering pacing pulses, defibrillation shocks or both, controlled by said means for characterizing the ventricular repolarization wave. In other words, the device implementing the teachings of the present invention may be:

- an external recorder able to be connected to external electrodes for collecting the surface ECG;
- an implanted device provided with electrodes for collecting subcutaneous ECG;
- an implanted device able to be connected to electrodes for collecting intracardiac or epicardiac EGM signals, and comprising means for reconstructing ECG signals based upon said collected EGM signals;
- an implanted device of the pacemaker and/or defibrillator type comprising means for delivering pacing pulses and/or defibrillation shocks, controlled by said means for characterizing the ventricular repolarization wave.

It should be understood that the means for performing the various functions of the apparatus of the present invention for performing the diagnosis includes the microprocessor, associated memory, and associated software for executing software instructions to process the collected, and preferably already digitized and filtered, ECG signals, whether collected directly or by reconstruction of collected EGM or other signals, as described herein. Advantageously, it should be understood that the apparatus for performing the assisted diagnosis may be employed in any of a number of implantable medical devices, as well as in devices that are not implanted, but can acquire the ECG data from a patient, e.g., by an implanted device (or by electrodes that are at least temporarily implanted in the patient).

Yet another aspect of the present invention is directed to a software control module (instruction set) that can be installed in an implantable device or in a non-implanted device such as a patient monitor or a programmer, or central station processing center, that can operate the machine to process the ECG signals for performing the diagnosis. One such software control module includes:

a) a first instruction set for isolating from the ECG signal, for each heart beat, an ST segment constituted by a succession of samples of the ventricular repolarization wave, taken within a time window of a predetermined period starting from a moment of window onset, defined by a time offset applied to a predetermined time origin;

b) a second instruction set for computing an elevation index of said segment compared to a predetermined reference level; and c) a third instruction set for analyzing over a succession of heart beats, the persistence and/or variation of said elevation index.

Of course, the above referenced advantageous subsidiary characteristics of the invention may be incorporated as instruction sets and become part of the software control module.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed in which like reference characters refer to like elements, and in which.

DETAILED DESCRIPTION OF THE INVENTION

One will now describe an example embodiment of the device according to the present invention.

Figure 1:
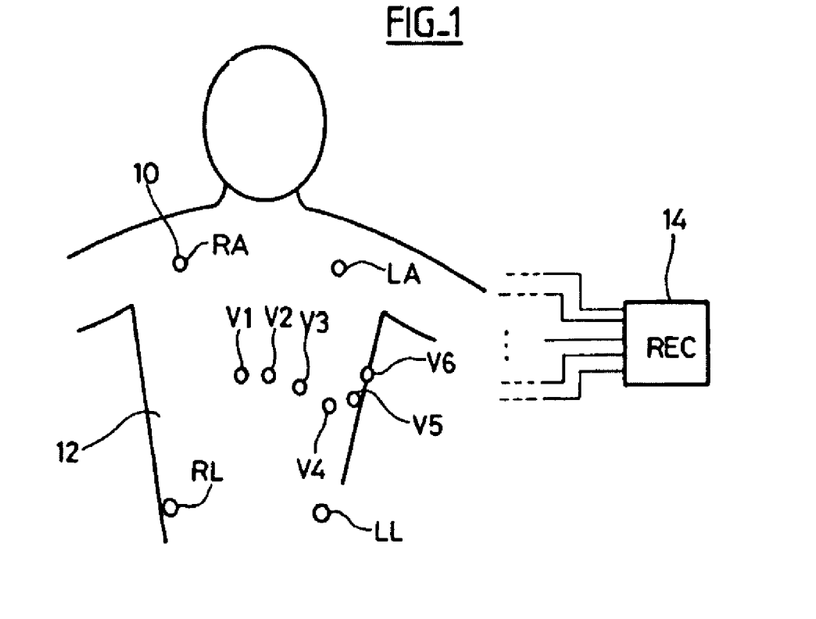
FIG. 1 is a schematic representing the thorax of a patient on which electrodes for collecting ECG signal have been applied, these electrodes being connected to an external recorder.

FIG. 1 schematically shows a situation wherein the invention is implemented by collecting an ECG signal by means of external surface electrodes applied on the thorax 12 of a patient.

Generally speaking, the heart electrical activity manifests on the surface of a patient's body through ECG signals that are collected by electrodes 10 that are positioned in particular locations of the patient's skin. These locations are conventionally designated as RA, LA, LL, and V1 to V6. The ECG signals are collected between predefined pairs of electrodes, each of these pairs determining a different derivation. The complete analysis of the ECG involves a set of twelve derivations, so that the heart electrical activity can be assimilated to a twelve-dimension vector that is varying over time: the bipolar (I, II, III) and unipolar (aVF, aVR, aVL) derivations allow to represent the electrical activity in the frontal plane, as the precordial derivations (v1 to v6) represent the electrical activity in the horizontal plane.

The signals from the various derivations are sampled, digitized and recorded by a device 14, which can be a device of the electrocardiograph type that can be used at a practitioner's office or in a hospital, or an ambulatory recorder of the Holter type ensuring recording of the data over a long period of time, typically over one or several days.

It should be understood that the present invention is not restricted to the analysis of a standard ECG along the twelve derivations, but can equally apply to ECG provided by a differed or smaller number of derivations. For the diagnosis of a syndrome such as Brugada syndrome or ERS, it is generally understood that the relevant derivations are the precordial derivations v1 to v6, preferably the standard derivations v1 to v3 which describe the electrical activity of the right ventricle. The Brugada syndrome and ERS are indeed pathologies that are related to a dysfunction of the transmembranous ionic current, which particularly manifests through modifications on the right ventricular ECG.

Figure 2:
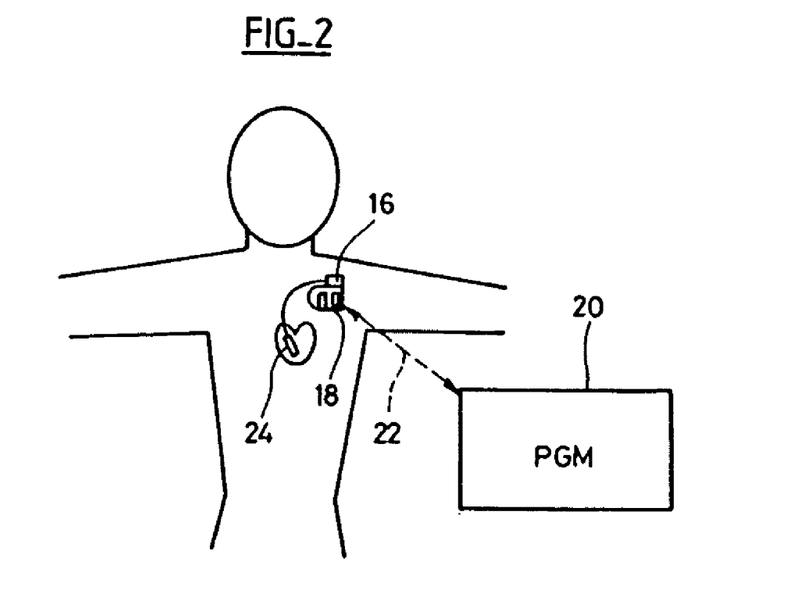
FIG. 2 is similar to FIG. 1, in the case when the ECG signals are collected from an implanted device such as a pacemaker.

FIG. 2 is similar to FIG. 1, but for the case when the ECG signals are collected by an active implantable medical device 16, typically a pacemaker or implantable defibrillator. The implantable device 16 can preferably be provided with electrodes 18 disposed on its housing, for collecting a subcutaneous ECG. The ECG is then obtained directly from the inside of the patient's body, instead of from surface electrodes applied on the skin, as in FIG. 1. The ECG thus obtained is processed and/or memorized in the implantable device 16, so as to be later read by an external device or programmer (PGM) 20 coupled to the implantable device 16 by means of a conventional non-galvanic link 22, such as an inductive link or radiofrequency (RF) link.

In an alternative embodiment, preferably for implanted devices not provided with electrodes for collecting subcutaneous ECG, it is possible to collect the intracardiac or epicardiac electrogram signals (EGM), by means of intracardiac or epicardiac electrodes 24. Such signals, directly issuing from the electrical activity of the cardiac cells, are typically used for controlling the implanted device and diagnosing some cardiac rhythm disorders requiring automatic scheduling of antitachycardia, antibradycardia or interventricular resynchronization therapies. However these ECG and EGM signals, even though having the same source (the electrical activity of the myocardium), present relatively different visual aspects. There are, however, some algorithms that can be used for the reconstruction of the surface ECG based upon EGM signals. For example, U.S. Pat. No. 5,740,811 and U.S. Pat. No. 6,980,850 describe techniques for emulating or synthesizing a surface ECG based upon EGM signals collected by an implanted device. One also may refer to U.S. patent application US 2008/0114259 (commonly assigned herewith to ELA Medical), which describes another technique for reconstructing an ECG based upon an EGM, allowing to palliate most of the deficiencies and limitations of the reconstruction algorithms previously proposed. Thus, the reconstructed ECG can be used within the scope of this invention, in the same manner as those ECG signal directly provided based upon external surface electrodes.

It is further possible to use a pair of dedicated electrodes, providing the most relevant information, and allowing by their own to provide the useful information of the v1 and v2 derivations, or to reconstruct the signal of such a derivation based upon an EGM through an appropriate reconstruction algorithm.

Whichever the method for collecting the signal representing the heart electrical activity (external electrodes, subcutaneous electrodes of ECG synthesized based upon an EGM, or otherwise), these signals are subjected to a preliminary processing of sampling, digitizing and filtering. Filtering may also include, in a manner already known per se, a filtering of the direct component (isoelectric line) and a low-pass filtering so as to eliminate the high frequency noises.

The ECG data can also be filtered so as to eliminate the heart beats of non-sinusal origin (ventricular or atrial ectopic beats). This operation can be carried out by analyzing the morphology of the cardiac complexes by means of algorithms, already known per se to persons of ordinary skill in the art, of the "Holter scanner" type.

Figure 3:
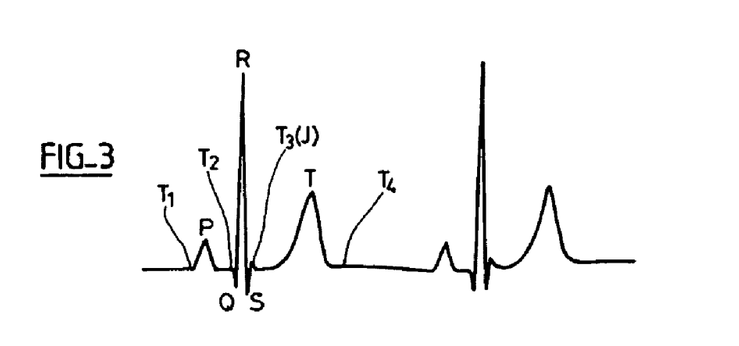
FIG. 3 shows the typical waveform of an ECG signal in a healthy patient, with the various characteristic points of this signal.

FIG. 3 shows the morphology of a heart beat of sinusal origin in a healthy patient. The atrial contraction (P wave) is followed by the ventricular contraction (QRS complex), then by a repolarization wave (T wave), which in a healthy subject has the shape of a bell ("bell-shaped"). The various corporal segments of the wave are defined between the moments $T_1$ (onset of P wave, or "P onset"), $T_2$ (onset of QRS complex, or "QRS onset"), $T_3$ or "J point" (end of QRS complex, or "QRS off-set), and $T_4$ (end of T wave, or "T offset").

The present invention more particularly relates to the analysis of the ST segment, that is: the segment defined by the $[T_3,T_4]$ interval. The time position (in abscissa) of the various points of this ST segment will be designated as a function of the number of milliseconds following the J point (moment $T_3$): for example "J+60" means a point of the wave located 60 milliseconds later than the J point. In other words, the onset of QRS complex (that is: the moment $T_2$) is usually easy to identify on all the derivations, whereas the end of QRS complex, at the junction with the ST segment, is usually difficult to characterize in an accurate manner, particularly on precordial derivations.

Figure 4:
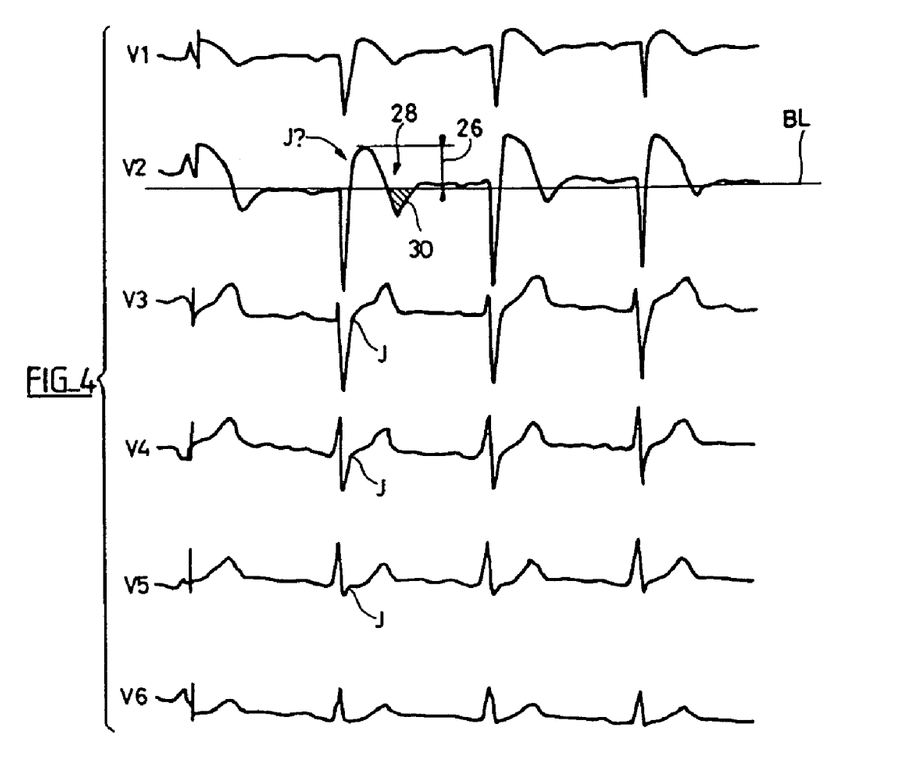
FIG. 4 shows the waveforms obtained on the various precordial derivations, for a patient presenting a Brugada syndrome.

FIG. 4 shows an example of signals obtained on the various precordial derivations v1 to v6, in a patient presenting a pathology of the type of Brugada syndrome (or ERS). In this example, the characteristic anomalies of the T wave are particularly visible on two of the precordial derivations (v1 and v2), with (i) a major elevation (as in 26) of the ST segment compared to the isoelectric or baseline BL, (ii) characteristic presence of a coved pattern on the T wave (as in 28), and (iii) trough followed by a negative T wave (as in 30). It should be observed that on the different derivations of the example shown in FIG. 4, the junction between the QRS complex and ST segment, that is: the J point, is well visible on the derivations v3 to v5—thus allowing characterization of the J point over time. But the junction is not on the derivations v1 and v2 which, precisely, present the T wave anomaly that is revealing the syndrome that is sought to be diagnosed.

Figure 5:
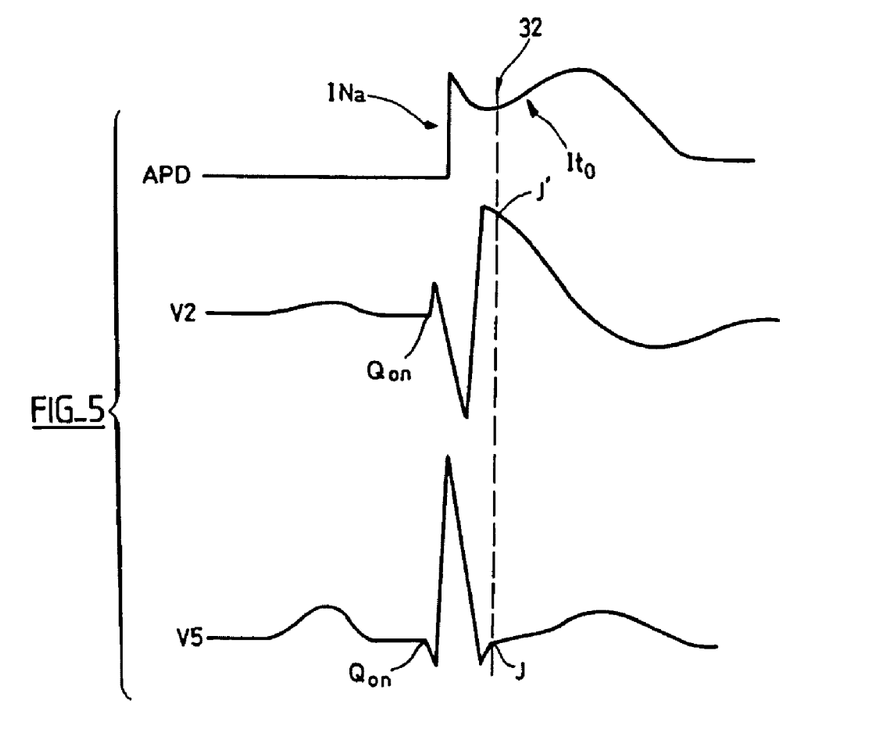
FIG. 5 shows the variations of the cellular wave potential, with simultaneous corresponding waveforms on the two precordial derivations.

FIG. 5 shows the variations of the cellular wave potential APD (Action Potential Duration), simultaneously with the corresponding waves on two precordial derivations v2 and v5. The comparison between the shapes of these two derivations highlights the phenomenon known as "interlead variability", or variability from one wave form to the other. Thus, the J point that is determined on the derivation v5, on which this point is well visible and characterized, provides on the derivation v2, a J' point with a time offset. Therefore, when the analysis is simply based upon the right precordial derivations, accurate estimation of the time position of the J point can be difficult.

The underlying mechanism of this phenomenon and ST elevation has been the subject of different assumptions. According to a first assumption, or "repolarization assumption", the amplification of the action potential (APnotch) in the right ventricle could be relating to a predominating current Ito towards the outside, not compensated by a current towards the inside, deficient, of sodium INa or calcium ICaions, these mechanisms being only occurring in the very first phases of the action potential. According to another assumption, or "conduction assumption", the ST segment elevation could be a consequence of a conduction delay due to a functional deficiency of the sodium channel, leading to a long persistence of repolarization in the right ventricle after the end of left ventricle repolarization. Any of these assumptions highlights the difficulty for accurately defining the J point in subjects who are presenting a Brugada syndrome or ERS, based upon the inventors' experimental observations.

Furthermore, the ST segment elevation phenomenon is a phenomenon that is relatively spread over time. Therefore, it cannot be meaningfully evaluated based upon one single signal sample. In other words, there is no possibility to obtain a reliable diagnosis based upon the measurement of the voltage level of a single point of the segment, considering the large variability of the phenomenon.

Figure 6:
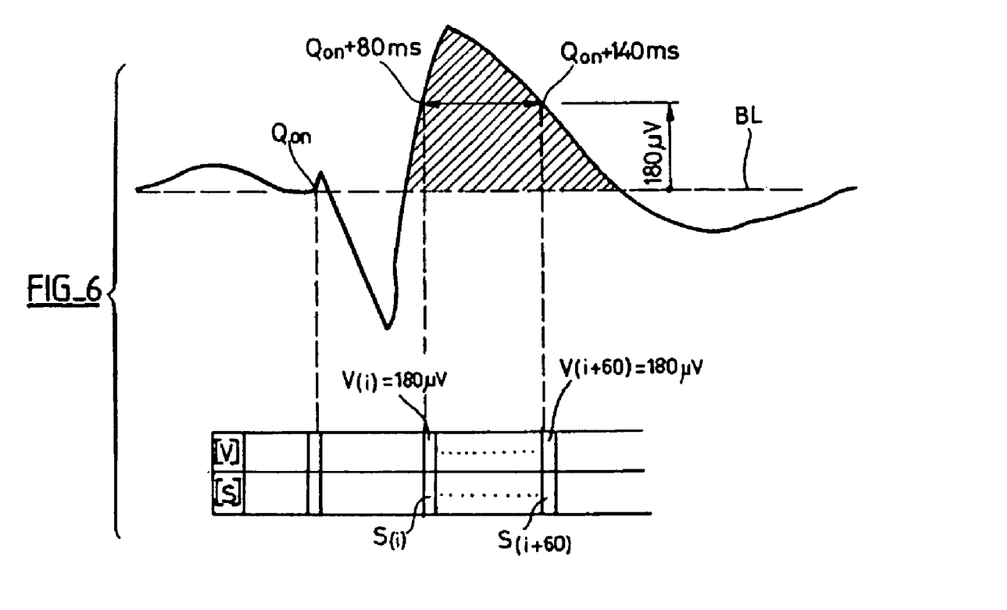
FIG. 6 shows the way a time window for analyzing the ST segment from the ECG signal of a precordial derivation is defined, with the corresponding matrix of digital data built up based upon the digitized samples.

In order to overcome this difficulty, and as shown in FIG. 6, the invention proposes to define a time window of a predetermined duration for the analysis of the ST segment. In accordance with one preferred embodiment of the present invention, the time positioning of this analysis window is not defined based upon the J point (whose position is not only difficult to determine, but also varies from one derivation from the other, as explained above), but based upon the $Q_{ON}$ point, corresponding to the QRS onset (point $T_2$ on FIG. 3). This point is accurately determinable: the moment $Q_{ON}$ of appearance of the QRS complex is defined as the earliest moment of rapid variation of the voltage compared to the isoelectric line BL, determined based upon the variations of the module $V_m$ of the vector defined based upon the various derivations (or one set of derivations among them, as for example the three precordial derivations v1, v2 and v3). This module is calculated as follows:

$$V_m = [(\text{Derivation1})^2 + (\text{Derivation2})^2 + \ldots + (\text{Derivation12})^2]^{1/2}$$

One can then define an analysis window starting, for example, at $t = Q_{ON}+80$ and ending at $t = Q_{ON}+140$, which has a total duration of 60 ms.

Of course these values are given as a typical example, which can be better adapted or parameterized as a function of particular cases or specific pathologies to be diagnosed. It shall be particularly observed that the average duration of a QRS segment in patients who are not presenting any structural cardiac pathology (as for patients presenting Brugada syndrome or ERS) is in the range of 100 ms, and that this duration relatively does not vary much as a function of heart rate. This duration is most of all a function of the patient's age, and can therefore be parameterized for a given patient.

The definition of an analysis window as described above allows quantizing the ECG anomalies in a zone essentially spreading from the end of depolarization to the beginning of repolarization in the right ventricle. As shown at the bottom of FIG. 6, the analysis window is associated to a matrix of digitized samples. This matrix actually corresponds to a table with two columns and n lines, with for each line i the rank $S_i$ of the sample and the value $V_i$ in microvolts, of the voltage measured at the corresponding point above the isoelectric line BL.

The number of samples of this matrix is directly related to the width of the window and sampling rate of the ECG. For a sampling rate of 1000 Hz (1 sample/ms) and for an analysis window width of 60 ms, the matrix will have two columns and 61 lines. In alternate embodiments, a subset of samples may be selected so as to reduce the number of variables, for example, one sample out of ten, i.e., the samples corresponding to the measured voltages at $Q_{ON}+80$, $Q_{ON}+90$, $Q_{ON}+100$, etc. are selected. Conversely, with a low sampling rate, one may operate an oversampling, in order to render a matrix that has the same size from one device to the other. This matrix can be subjected to various processing and computing operations, as a function of the sought diagnosis. The matrix can first be transformed through applying various mathematical functions, for example, a principal component analysis (PCA), a Karhunen-Loeve transform (KLT), or a derivative calculation (indeed a derivative allows analyzing the descending slope of ST segment). The right precordial derivations also provide a tri-dimensional signal v1 v2 v3 that can be processed through singular value decomposition so as to obtain a set of independent orthogonal vectors, the vector presenting the highest eigenvalue being possibly used for calculating a matrix based upon PCA analysis.

In addition to the voltage parameter (elevation of the ST segment above the isoelectric line BL), it is also possible to analyse the surface area data corresponding to a product voltage×time (hatched surface on the waveform in FIG. 6). Indeed it is known that such a variable can be useful for the detection of a left ventricular hypertrophy and for the quantification of ventricular repolarization in the congenital form of long QT syndrome. In this present case, the surface area is given by the product of the different voltages (amplitudes in microvolts) by the duration of the analysis window in milliseconds, the resulting unit being mV·ms. This calculation allows transforming the matrix into a unique parameter constituting a quantified index representative of the ST segment elevation for the considered waveform.

This index is particularly relevant for assisted diagnosis of Brugada syndrome or ERS. Indeed, the electrical activity of the right ventricular wall in patients presenting such a syndrome is a complex phenomenon, and experimental studies have shown the presence of electrical heterogeneity between the endocardium, epicardium and the different sites. The integration of ECG signal by a product time * voltage better reflects the cell deficiencies than an isolated voltage value at a predefined time point.

Some other types of morphologies may also be characterized, for example correlated with the amplitude (maximum, minimum), or of temporal nature (presence of an early or late phenomenon within the analysis window) as long as the repolarization process can vary along the considered time scale.

It is also possible, through analyzing the voltage variations within the analysis window, to seek within the ST segment, the presence of a coved pattern that is characteristic of Brugada syndrome or ERS, for example, by seeking whether: $V(Q_{on}+80) > V(Q_{on}+90) > \ldots > V(Q_{on}+140)$. Or by seeking whether: $dV/dt \,[Q_{on}+80; Q_{on}+140] < 0$ and $|dV/dt \,[Q_{on}+80;$ $Q_{on}+140]|>$ predetermined threshold, the whole being followed by a negative wave (V<0 in the area 30 of FIG. 4).

These various treatments and computations allow, for each heart beat, to calculate an elevation index of the ST segment compared to a predetermined reference.

For the purpose of diagnosis, it is then necessary to analyze the persistence and/or variation of this index over a succession of heart beats. Indeed, as it was described above, in the case of Brugada syndrome or ERS, the ST segment presents a great variability from one beat to the other.

In a preferred embodiment of this invention, such analysis of the middle/long term variations of this index is preceded by a classification of the index values obtained for each beat. The distribution of obtained index values can preferably be operated between different predefined classes as a function of a given parameter, for example heart rate (more particularly in a bradycardia situation). In such case, all the index values obtained when the rate is 100 bpm, for instance, are gathered, as well as all the values obtained for a rate of 75 bpm, all those obtained for a rate of 50 bpm, etc.

Some parameters other than heart rate may be used for defining the different classes, include, but are not strictly limited to:
the RR interval,
the type of period of the day (day/night/meal, . . . ),
the level of activity of the patient,
the patient's body temperature (in the case temperature sensors are used),
the nature: paced or natural of the patient's heart beat,
the sinusal or extrasystolic character of the heart beat,
the existence of a drug treatment (for example quinidine, which can be prescribed in place of a cardiac pacemaker),
or combinations of all these parameters, for example classes defined by the product rate*period, etc.

The analysis of persistence or variation of the ST segment elevation index is then operated separately for each of the classes. This allows eventually isolating some particular conditions of appearance of Brugada syndrome or ERS, with a quantizing allowing to evaluate a more or less serious risk of occurrence of a pathologic episode.

Figure 7:
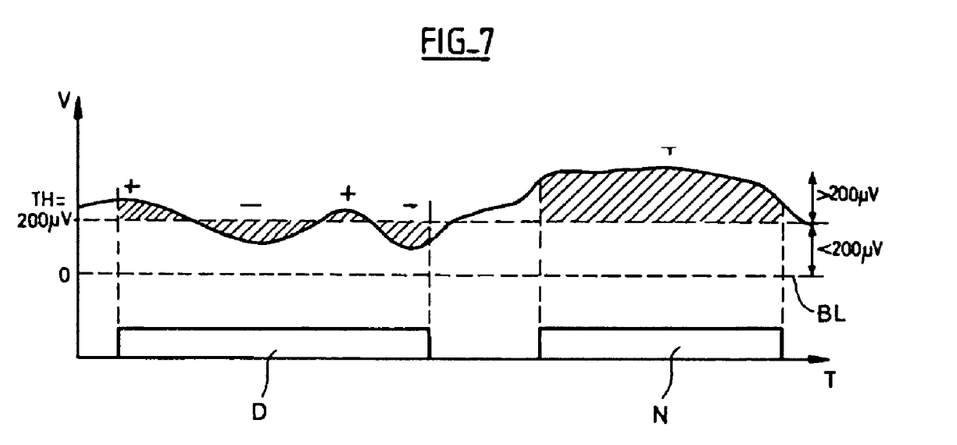
FIG. 7 shows the variations, over a 24-hour period, of an index of ST segment elevation compared to a predetermined criterion.

As shown in FIG. 7, the variations over time of the ST segment elevation index (typically over a period of at least 24 hours) may provide information on the evolution of a risk of serious episode, such risk being reflected by a parameter designated as "Brugada load" (or "ERS load"). It can preferably be seen on the example of FIG. 7 that during diurnal periods (D), the ST segment elevation above the isoelectric line BL typically varies around a critical threshold TH of 200 µV, but that during nocturnal periods (N), the elevation notably increases beyond this same threshold. The sign changes of the parameter above and below the threshold TH thus allow to detect the appearance of severe Brugada or ERS episodes (typically: during nocturnal period for Brugada syndrome), so as to trigger any appropriate preventive action.

Figure 8:
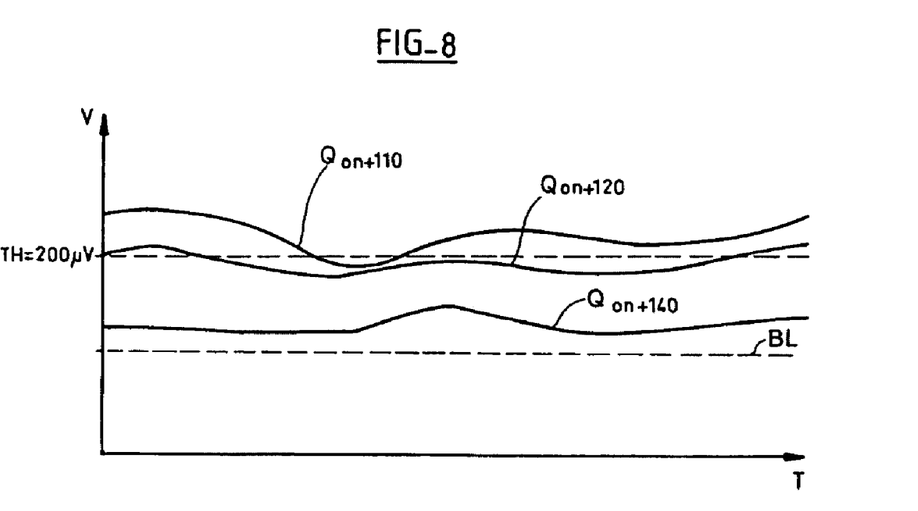
FIG. 8 shows the variations, over time, of this elevation index for different duration of the analysis time window.

In FIG. 8 are represented the variations along time of the Brugada loads obtained when varying the width of the analysis window, with a same onset bound but with an offset bound set to $Q_{on}+110$, $Q_{on}+120$ and $Q_{on}+140$ ms. The different values are displayed separately, revealing more or less significant variations in the different cases. Such display notably allows the practitioner to parameterize in an optimal manner, the analysis window width, more or less long, as a function of each patient subjected to the diagnosis.

A clinical trial was carried out by applying the teachings of this invention, which demonstrated the relevance of the characterization, performed following the method described above, of the ST segment elevation for the purpose of diagnosing patients presenting Brugada syndrome, whether they symptomatic or asymptomatic. The trial has been carried out in 32 healthy reference patients (16 men, of an average age of 50.3±21.6 years), and 34 patients presenting Brugada syndrome (15 symptomatic patients, and 19 asymptomatic patients: 30 men, of an average age of 46.4±11.4 years).

A 12-derivation Holter ECG was collected for all the population of patients. The collected QRST complexes have been averaged each minute, giving 1440 ECG waveforms over the 24 hours of recording. An analysis window has been defined, beginning at $t=Q_{on}+80$ ms and ending at $t=Q_{on}+140$ ms. The following parameters have been collected: maximum elevation of ST segment, time position of this maximum compared to $Q_{on}$, slope of ST segment and amplitude at point T. The data measured on derivations v1 and v2 are shown in TABLE 1 below (mean value and standard variation). Compared to asymptomatic patients, the symptomatic patients do not show a significant trend toward a greater elevation of the maximum of ST segment. The QRST diagram of symptomatic patients is characterized by a greater prematurity of the maximum of ST segment, a higher descending slope of ST segment and a more negative voltage for the position of point T. Thus a basis for making a diagnosis is provided.

TABLE 1

| | | Healthy N = 32 | Asymptomatic N = 19 | Symptomatic N = 15 |
|---|---|---|---|---|
| v1 | Max ST elevation (µV) | 56 ± 32 | 202 ± 121 * | 206 ± 130 * |
| | Max ST position ($Q_{on}$ + xx) | 128 ± 17 | 109 ± 13 * | 101 ± 14 * |
| | slope (µV/ms) | 0.3 ± 0.4 | −2.1 ± 2.0 * | −3.0 ± 2.7 * |
| | T amplitude (µV) | 31 ± 118 | −85 ± 115 * | −190 ± 158 * † |
| v2 | Max ST elevation (µV) | 133 ± 88 | 270 ± 119 * | 310 ± 152 * |
| | Max ST position ($Q_{on}$ + xx) | 136 ± 10 | 118 ± 15 * | 108 ± 16 * † |
| | slope (µV/ms) | 1.2 ± 1.0 | −1.2 ± 2.4 * | −3.4 ± 3.0 * † |
| | T amplitude (µV) | 473 ± 275 | 165 ± 228 * | −52 ± 253 * † |

* $p < 0.05$ post-test vs. healthy patients
† $p < 0.05$ post-test vs. asymptomatic patients Regarding the software-related aspects thereof, the functionality and processes of the present invention can be implemented by an appropriate programming of the software of a known external programmer or implantable device, for example, a pacemaker or defibrillator/cardioverter, or a Holter monitoring device.

The invention can preferably be applied to the commercial implantable devices marketed by ELA Medical, Montrouge France, such as Symphony and ELA Rhapsody brand pacemakers and comparable commercial and/or proprietary devices of other manufacturers. These devices are equipped with programmable microprocessors, including circuits intended to acquire, format and process electrical signals collected by implanted electrodes and various sensors, and deliver pacing pulses or defibrillation pulses to implanted electrodes as appropriate to deliver a therapy in response to the detection of an ST elevation associated with a Brugada Syndrome or ERS. It is also possible to upload towards these devices, by telemetry, pieces of software (i.e., a software control module) that will be stored in internal memory and run so as to implement the features and functionality of the invention, as described herein. Implementing the features of the invention into these devices is believed to be easily feasible by a person of ordinary skill in the art, and will therefore not be described in detail in this document.

As noted, the present invention can however be implemented not only within an implantable device, but also within an external programmer used by a practitioner, so as to download and analyze the heart signals collected and memorized by an implantable device. This invention can notably be applied to retrofit the ORCHESTRA brand programmers commercialized by ELA Medical, Montrouge, France, the assignee hereof, intended to program implantable devices such as SYMPHONY, REPLY, OVATIO, and PARADYM brand devices also commercialized by ELA Medical. These programmers are microcomputers specifically configured so as to implement the programming features, in conjunction with a telemetry head connected to the computer and coupled to these implantable devices through inductive or radiofrequency (RF) communications protocols in a known manner.

Adapting these devices for implementing the features of this invention by software programs of the functions described herein is believed to be easily within the abilities of a person of ordinary skill in the art, and will therefore not be described in detail in this document.

In another implementation, the present invention is also implemented in a home monitoring monitor, which is a particular type of external programmer, the operation of which is typically totally automated and does not require the intervention of a practitioner, notably to allow remote transmission towards a distant site at regular intervals, for example, on a daily basis, of the collected data, for further analysis and patient follow-up. The present invention can equally be implemented level with the data server of said distant remote site, the raw ECG or EGM data (with or without digitization and filtering) thus being directly uploaded towards this server, with no preliminary processing and stored in memory therein. The processing can then be performed by the server or terminal (PC or programmer) connected thereto.

Although the detailed description of the invention has been discussed in the context of an apparatus, it should be understood that the present invention applies equally to a method and to a software control module that operates on ECG data, whether collected directly or by reconstruction, to perform the functionality required to obtain the waveforms to perform the diagnosis. Indeed, one skilled in the art will appreciate that the present invention can be practical by other than the embodiments described herein, which are presented for purposes of illustration and not of limitation.

We claim:

1. A device for an assisted electrocardiologic diagnosis comprising means for characterizing the ventricular repolarization wave of an ECG signal collected from a patient, said ECG signal having been preliminarily sampled and digitized, said device comprising:

means for determining the time position of a moment of appearance of the QRS complex on said ECG signal for each heart beat;

extracting means for isolating out of the ECG signal, for each heart beat, an ST segment comprising a succession of samples of the ventricular repolarization wave, taken within a time window of a predetermined width, said width having a moment of window onset, said moment of window onset having a time offset from a predetermined temporal origin; wherein said predetermined temporal origin comprises said determined moment of appearance of the QRS complex;

quantizing means for computing an elevation index of said ST segment compared to a predetermined reference level; and means for analyzing over a succession of heart beats, selected from the group consisting of the persistence the elevation index and the variation of the elevation index.

2. The device of claim 1, wherein said time offset from the predetermined temporal origin ranges from between 60 and 100 ms.

3. The device of claim 1, wherein said predetermined width of the time window ranges from between 50 and 80 ms.

4. The device of claim 1, wherein said quantizing means further comprises means for creating a matrix providing, for a series of samples (S,) taken within said time window, the amplitude (V,) of corresponding samples of the ECG signal.

5. The device of claim 4, wherein said series of samples is a subset of the samples of said succession of samples of the ventricular repolarization wave.

6. The device of claim 4, wherein said device comprises means for concurrently analyzing a plurality of ECG signals coming from different derivations, and means for applying to the matrix a mathematical transform selected from among the group consisting of:

a principal component analysis, a KarhunenLoeve transform, and a derivative calculation.

7. The device of claim 1, wherein said quantizing means further comprises integrating means for computing the surface area defined by the ECG signal over the width of said time window, for determining the elevation index.

8. The device of claim 1, wherein said analyzing means comprises means for evaluating an average level of the elevation index based upon at least one of: during a given duration and over a given number of heart beats, and for analyzing the long term variations of the elevation index around this average level.

9. The device of claim 8, wherein the analyzing means comprises classifying means for distributing into a plurality of classes the successive values of said elevation index collected based upon at least a given duration and a given number of successive heart beats, said distribution into classes being operated as a function of a parameter measured by the device or known thereby.

10. The device of claim 9, further comprising means for analyzing at least one of a persistence and a variation of the elevation index, separately for each class.

11. The device of claim 9, wherein said parameter is one selected from among the group comprising of: heart rate, RR interval, diurnal nocturnal or prandial of the moment of analysis, the patient's level of activity, the patient's body temperature, the natural or paced nature of the heart beat, the sinusal or extrasystolic character of the heart beat, and the existence of a drug treatment.

12. The device of claim 1, wherein said analyzing means comprises means for searching within the ST segment, the presence of a coved pattern that is characteristic of a one of a Brugada syndrome and an Early Repolarization Syndrome.

13. The device of claim 1 further comprising a graphical display of the variations over time of said elevation index.

14. The device of claim 1, wherein said analyzing means further comprises means for providing information of assisted diagnosis comprising a risk marker.

15. The device of claim 14, wherein the information comprising a risk marker is provided when the elevation index computed by the quantizing means is greater than a predefined threshold during a predetermined duration.

16. The device of claim 14, wherein the information comprising a risk marker is provided when the elevation index computed by the quantizing means is greater than a predefined threshold over a given number of heart beats.

17. The device of claim 14, wherein the information comprising a risk marker is provided when the elevation index computed by the quantizing means is greater than a predefined threshold during a predetermined duration and over a given number of heart beats.

18. The device of claim 14, wherein said analyzing means further comprises means for concurrently analyzing a plurality of ECG signals coming from more than two different precordial derivations, and wherein the information comprising a risk marker is provided when the elevation index computed by said quantizing means is greater than a predefined threshold during a predetermined duration, for ECG signals coming from at least two of said precordial derivations.

19. The device of claim 14, wherein said analyzing means further comprises means for concurrently analyzing a plurality of ECG signals coming from more than two precordial derivations, and wherein the information comprising a risk marker is provided when the elevation index computed by said quantizing means is greater than a predefined threshold over a given number of heart beats, for ECG signals coming from at least two of said precordial derivations.

20. The device of claim 14, wherein said device is able to concurrently analyze a plurality of ECG signals coming from different precordial derivations, and wherein the information comprising a risk marker is provided when the elevation index computed by said quantizing means is greater than a predefined threshold during a predetermined duration and over a given number of heart beats, for ECG signals coming from at least two of said precordial derivations.

21. The device of claim 1, wherein said device is an external recorder able to be connected to external electrodes for collecting cutaneous ECG.

22. The device of claim 1, wherein said device is an implanted device comprising electrodes for collecting a subcutaneous ECG.

23. The device of claim 1, wherein said device is an implanted device able to be connected to electrodes for collecting intracardiac or epicardiac EGM signals, said device further comprising means for reconstructing ECG signals based upon said collected EGM signals.

24. The device of claim 1, wherein said device is an implanted device of the pacemaker, defibrillator or pacemaker/defibrillator or resynchronization device, said device further comprising means for delivering pacing pulses, defibrillation shocks or both, controlled by said means for characterizing the ventricular repolarization wave.

* * * * *